(12) United States Patent
Yuan et al.

(10) Patent No.: US 11,905,224 B2
(45) Date of Patent: Feb. 20, 2024

(54) **METHOD FOR FULLY RECYCLING KITCHEN WASTE BY USING *HERMETIA ILLUCENS* L. AND AEROBIC MICROORGANISMS**

(71) Applicants: NANJING UNIVERSITY, Jiangsu (CN); LISHUI INSTITUTE OF ECOLOGICAL ENVIRONMENT, NANJING UNIVERSITY, Jiangsu (CN)

(72) Inventors: Zengwei Yuan, Jiangsu (CN); Mingjin Cheng, Jiangsu (CN); Xiang Cheng, Jiangsu (CN); Shiwen Zhang, Jiangsu (CN)

(73) Assignees: NANJING UNIVERSITY, Jiangsu (CN); LISHUI INSTITUTE OF ECOLOGICAL ENVIRONMENT, NANJING UNIVERSITY, Jiangsu (CN)

( * ) Notice: Subject to any disclaimer, the term of this patent is extended or adjusted under 35 U.S.C. 154(b) by 0 days.

(21) Appl. No.: 18/308,685

(22) Filed: Apr. 28, 2023

(65) Prior Publication Data
US 2023/0331637 A1    Oct. 19, 2023

Related U.S. Application Data

(63) Continuation of application No. PCT/CN2022/095814, filed on May 28, 2022.

(30) Foreign Application Priority Data

Apr. 15, 2022  (CN) .......................... 202210397668.9

(51) Int. Cl.
*C05F 17/05*    (2020.01)
*B09B 3/80*    (2022.01)
(Continued)

(52) U.S. Cl.
CPC ............ *C05F 17/05* (2020.01); *A01K 67/033* (2013.01); *B09B 3/30* (2022.01); *B09B 3/80* (2022.01)

(58) Field of Classification Search
CPC ........... B09B 3/30; B09B 3/80; A01K 67/033; C05F 17/05; A23K 10/12; A23K 10/26;
(Continued)

(56) References Cited

U.S. PATENT DOCUMENTS 10,588,331 B2 *  3/2020  Popa ...................... A23K 10/12
11,760,700 B2 *  9/2023  Ma .......................... C05F 17/05
                                                                    71/23
(Continued)

FOREIGN PATENT DOCUMENTS

CN       103736709       4/2014
CN       105906390       8/2016
(Continued)

*Primary Examiner* — Joseph C Rodriguez
(74) *Attorney, Agent, or Firm* — JCIPRNET

(57) ABSTRACT

The present application provides a method for fully recycling kitchen waste by using *Hermetia illucens* L. and aerobic microorganisms. The method includes first performing solid-liquid separation on the kitchen waste; then using the filtrate obtained through separation to feed young larvae of *Hermetia illucens* L. to convert salt in the filtrate into body fluid of *Hermetia illucens* L. in a larval stage, and using the kitchen waste filter residue to feed $2^{nd}$-$6^{th}$-instar larvae of *Hermetia illucens* L. respectively; separating insects and insect feces residue in a timely manner, so as to reduce a salt content of insect feces and improve transabdominal transformation efficiency of *Hermetia illucens* L. and quality of the insect manure; and finally implementing full resource utilization through aerobic composting and insect drying and sterilization treatment.

7 Claims, 2 Drawing Sheets

(51) Int. Cl.
*B09B 3/30* (2022.01)
*A01K 67/033* (2006.01)

(58) Field of Classification Search
CPC ........ A23K 10/30; A23K 10/37; A23K 20/10;
A23K 50/90; B03C 1/30; B07B 2230/01
See application file for complete search history.

(56) References Cited

U.S. PATENT DOCUMENTS

2017/0265496 A1* 9/2017 Popa ...................... A23K 10/12
2022/0312797 A1* 10/2022 Pipan ..................... A23K 10/20

FOREIGN PATENT DOCUMENTS

| CN | 112741047 | | 5/2021 | | |
|---|---|---|---|---|---|
| CN | 112741047 A | * | 5/2021 | | |
| CN | 113575517 | | 11/2021 | | |
| CN | 218108832 U | * | 12/2022 | | |
| WO | WO-2019219041 A1 | * | 11/2019 | ............. | A23K 10/12 |

* cited by examiner

METHOD FOR FULLY RECYCLING KITCHEN WASTE BY USING *HERMETIA ILLUCENS* L. AND AEROBIC MICROORGANISMS

CROSS-REFERENCE TO RELATED APPLICATION

The present application is a continuation of PCT application No. PCT/CN2022/095814, filed on May 28, 2022, which claims the priority benefit of China Application No. 202210397668.9, filed on Apr. 15, 2022. The entirety of each of the above mentioned patent applications is incorporated by reference herein and made a part of this specification.

BACKGROUND

Technical Field

The present application relates to the field of resource utilization of organic solid waste, and in particular, to a method for fully recycling kitchen waste by using *Hermetia illucens* L. and aerobic microorganisms.

Description of Related Art

Kitchen waste has a large generation amount and easily rots and stinks. Implementing its resource and high-value utilization is a key goal to promote sustainable development of cities. Among existing kitchen waste recycling technologies, heat treatment technologies such as incineration and pyrolysis need a lot of energy and cause secondary pollution, and thus the technologies are gradually replaced by mature technologies such as anaerobic fermentation for biogas production, and aerobic composting. However, the salt content of kitchen waste in China is as high as 0.4%-2.0%, and direct aerobic composting of the kitchen waste may lead to an excessive salt content, making the quality of compost products not up to standard, or if anaerobic fermentation of the kitchen waste is directly performed for biogas production, it is difficult to treat biogas residue. Due to excessive salt in kitchen waste, these two mainstream processes need to be equipped with an additional salt removal device, which leads to an increase in operating costs and the difficulty in secondary waste treatment. Therefore, it can be learned that the salt content in high-oil and high-salt kitchen waste has become a key obstacle to its full resource utilization.

*Hermetia illucens* L. has certain effects in biotransformation of kitchen waste, but currently problems in the following aspects exist in existing technologies: (1) A large amount of high-salt wastewater is produced during transformation by *Hermetia illucens* L., which requires adding of a complicated wastewater treatment project, with high overall technical costs and complicated engineering; (2) the impact of adjustment of oil, salt, and water in kitchen waste on the growth of *Hermetia illucens* L. is neglected, and treatment efficiency is low; (3) the salt in insect feces is not effectively reduced, and quality of compost products is still not up to standard, making it difficult to sell; and (4) the oxygen content of compost material layers cannot be accurately controlled, and it is difficult to prevent anaerobic reaction of compost materials, which produces odor and pollutes the environment, and prolongs its treatment cycle and causes a large amount of nitrogen loss. It is difficult to implement full resource utilization of kitchen waste by using existing treatment technologies.

SUMMARY

In view of the disadvantages in existing technologies, the present application provides a method for fully recycling kitchen waste by using *Hermetia illucens* L. and aerobic microorganisms. In the present application, by feeding young larvae with an oil-containing and salt-containing filtrate in kitchen waste, most of the salt can be transferred to body fluid of *Hermetia illucens* L. larvae, and organic matter such as fat and proteins in the kitchen waste can be transformed into biological proteins during subsequent biotransformation. The process of the present application can effectively reduce the salt content of insect feces and treatment costs of high-salt wastewater, and has great industrialization potential. The present application specifically adopts the following technical solutions.

To achieve the foregoing objective, a method for fully recycling kitchen waste by using *Hermetia illucens* L. and aerobic microorganisms is first put forward. The method includes the following steps: step 1: performing solid-liquid separation pretreatment on kitchen waste to obtain kitchen waste filter residue with a water content not greater than 75% and an oil-containing and salt-containing filtrate, and crushing and homogenizing the kitchen waste filter residue to form slurry with a particle size of 3-8 mm; step 2: mixing wheat bran with the oil-containing and salt-containing filtrate to feed young larvae hatched from eggs; after the young larvae grow into *Hermetia illucens* L. larvae, using the kitchen waste filter residue instead to feed the *Hermetia illucens* L. larvae, and regularly screening a mixture of the *Hermetia illucens* L. larvae and insect feces to obtain oversize *Hermetia illucens* L. larvae and undersize insect feces; and step 3: sending the separated insect feces to an aerobic microbial degradation apparatus for aerobic composting to obtain an organic fertilizer; and after the *Hermetia illucens* L. larvae grow to the $5^{th}$-$6^{th}$ instars, screening out *Hermetia illucens* L. insects, and drying and sterilizing the *Hermetia illucens* L. insects to obtain dried insects.

Optionally, in the method for fully recycling kitchen waste by using *Hermetia illucens* L. and aerobic microorganisms according to any one of the foregoing implementations, in step 1, inert impurities in the kitchen waste are removed by magnetic separation and separation by using a roller, and then solid-liquid separation is performed; a water content of the kitchen waste filter residue is controlled to be no more than 75% by pressure filtration, so that salinity is adjusted to 2.8%-3.2%, and an oil content is controlled at 2.6%-15%; and through oil-water separation after standing, the oil content of the oil-containing and salt-containing filtrate is controlled at 3.4%-15%, and then the salinity is 5.5%-6.5%.

Optionally, in the method for fully recycling kitchen waste by using *Hermetia illucens* L. and aerobic microorganisms according to any one of the foregoing implementations, the water content of the kitchen waste filter residue is controlled to be no more than 70%, the salinity thereof is 3%, and the oil content thereof is 5.2%; and after standing, through oil-water separation of the oil-containing and salt-containing filtrate, the oil content of the oil-containing and salt-containing filtrate is controlled at 9.2%, and the salinity thereof is adjusted to 5.8%.

Optionally, in the method for fully recycling kitchen waste by using *Hermetia illucens* L. and aerobic microorganisms according to any one of the foregoing implementations, in step 2, the mass ratio of the oil-containing and salt-containing filtrate, the wheat bran, and the *Hermetia illucens* L. eggs is (32-35):(18-20):1, and the humidity of the mixed material is controlled at 60%-70%; and after the young larvae of *Hermetia illucens* L. are fed for 5-7 days, $2^{nd}$-$3^{rd}$-instar *Hermetia illucens* L. larvae are obtained.

Optionally, in the method for fully recycling kitchen waste by using *Hermetia illucens* L. and aerobic microorganisms according to any one of the foregoing implementations, the mass ratio of the oil-containing and salt-containing filtrate, the wheat bran, and the *Hermetia illucens* L. eggs is 32:20:1, and the humidity of the mixed material is controlled at 65%; and after the young larvae of *Hermetia illucens* L. are fed for 5 days, $2^{nd}$-instar *Hermetia illucens* L. larvae are obtained, and then the *Hermetia illucens* L. larvae are fed with the kitchen waste filter residue slurry.

Optionally, in the method for fully recycling kitchen waste by using *Hermetia illucens* L. and aerobic microorganisms according to any one of the foregoing implementations, in step 2, after the young larvae of *Hermetia illucens* L. grow into $2^{nd}$-$3^{rd}$-instar *Hermetia illucens* L. larvae, the *Hermetia illucens* L. larvae are fed evenly in batches at a ratio of correspondingly adding 900-1100 g of kitchen waste filter residue slurry to every gram of *Hermetia illucens* L. larvae every day, exhausting and turning are regularly performed to control temperature and humidity, and the *Hermetia illucens* L. larvae and insect feces obtained through transabdominal transformation of the kitchen waste filter residue by the *Hermetia illucens* L. larvae are screened every day to obtain oversize *Hermetia illucens* L. larvae for continued feeding with the kitchen waste, and undersize insect feces for composting.

Optionally, in the method for fully recycling kitchen waste by using *Hermetia illucens* L. and aerobic microorganisms according to any one of the foregoing implementations, in step 2, the feeding evenly in batches at a ratio of correspondingly adding 900-1100 g of kitchen waste filter residue slurry to every gram of *Hermetia illucens* L. larvae every day includes: evenly adding 225-366 g of kitchen waste filter residue slurry to each gram of *Hermetia illucens* L. larvae at intervals of 6-8 hours for 3-4 times every day.

Optionally, in the method for fully recycling kitchen waste by using *Hermetia illucens* L. and aerobic microorganisms according to any one of the foregoing implementations, in step 2, the feeding evenly in batches at a ratio of correspondingly adding 900-1100 g of kitchen waste filter residue slurry to every gram of *Hermetia illucens* L. larvae every day includes: evenly adding 300-366 g of kitchen waste filter residue slurry to each gram of *Hermetia illucens* L. larvae at intervals of 6 hours for 3 times every day.

Optionally, in the method for fully recycling kitchen waste by using *Hermetia illucens* L. and aerobic microorganisms according to any one of the foregoing implementations, in step 2, a standard for regularly exhausting and turning to control temperature and humidity is that exhausting is performed for 20 minutes every hour, turning is performed once every 6 hours, so that the temperature of a feeding layer is controlled to be kept at 28-32° C., the air humidity in a transabdominal transformation biological reaction chamber is controlled to be kept at 60%, and an oxygen content of the feeding layer is kept at 15% or above.

Optionally, in the method for fully recycling kitchen waste by using *Hermetia illucens* L. and aerobic microorganisms according to any one of the foregoing implementations, in step 2, within 10-12 days after the *Hermetia illucens* L. larvae are added, the mixture of the *Hermetia illucens* L. insects and the insect feces is screened every day, and the *Hermetia illucens* L. larvae are returned to the transabdominal transformation biological reaction chamber for continued feeding; and in 13-14 days after the *Hermetia illucens* L. larvae are added, the *Hermetia illucens* L. larvae are starved, the mixture of the insects and the insect feces is screened, and the *Hermetia illucens* L. insects are dried and sterilized to obtain the dried insects.

Beneficial Effects

According to the present application, solid-liquid separation pretreatment is first performed on kitchen waste to obtain kitchen waste filter residue and an oil-containing and salt-containing filtrate; then the oil-containing and salt-containing filtrate and the kitchen waste filter residue are used as resources based on quality, the oil-containing and salt-containing filtrate is mixed with wheat bran to feed young larvae of *Hermetia illucens* L., and the solid kitchen waste filter residue undergoes transabdominal transformation by $2^{nd}$-$6^{th}$-instar *Hermetia illucens* L. larvae to improve utilization efficiency of organic matter therein; finally, *Hermetia illucens* L. insects are separated from insect feces residue, the insect feces residue is degraded by aerobic microorganisms to produce an organic fertilizer, and the insects are dried and sterilized to produce dried insects, thereby implementing full resource utilization of the kitchen waste. According to the present invention, it is for the first time to put forward cooperation of principles of transabdominal transformation by *Hermetia illucens* L. and aerobic microbial degradation, to implement full resource transformation of kitchen waste, which overcomes the following problems in the existing transformation process: (1) The filtered oil-containing and salt-containing filtrate is used as high-salt wastewater, which has high treatment costs and is difficult to treat; if the filtered oil-containing and salt-containing filtrate is directly used as feed for *Hermetia illucens* L., the salt content of insect feces may be too high to meet a fertilizer standard, and resource utilization cannot be implemented; (2) a poor ratio of water, salt and oil in kitchen waste leads to low palatability, transabdominal transformation efficiency of *Hermetia illucens* L. is low, *Hermetia illucens* L. grows slowly, and feeding costs are high; and (3) an anaerobic environment in the composting process leads to generation of nitrogen-containing odor, which leads to a loss of nitrogen during transformation by *Hermetia illucens* L. and affects quality of the fertilizer, and the like.

Other features and advantages of the present application are set forth in the subsequent description, and in part become obvious from the description, or are learned by implementing the present application.

BRIEF DESCRIPTION OF THE DRAWINGS

Accompanying drawings are intended to provide a further understanding of the present application, and constitute a part of the description. With the embodiments of the present application, the accompanying drawings are intended to explain the present application, and do not constitute a limitation on the present application. In the drawings.

DESCRIPTION OF THE EMBODIMENTS

Figure 1:
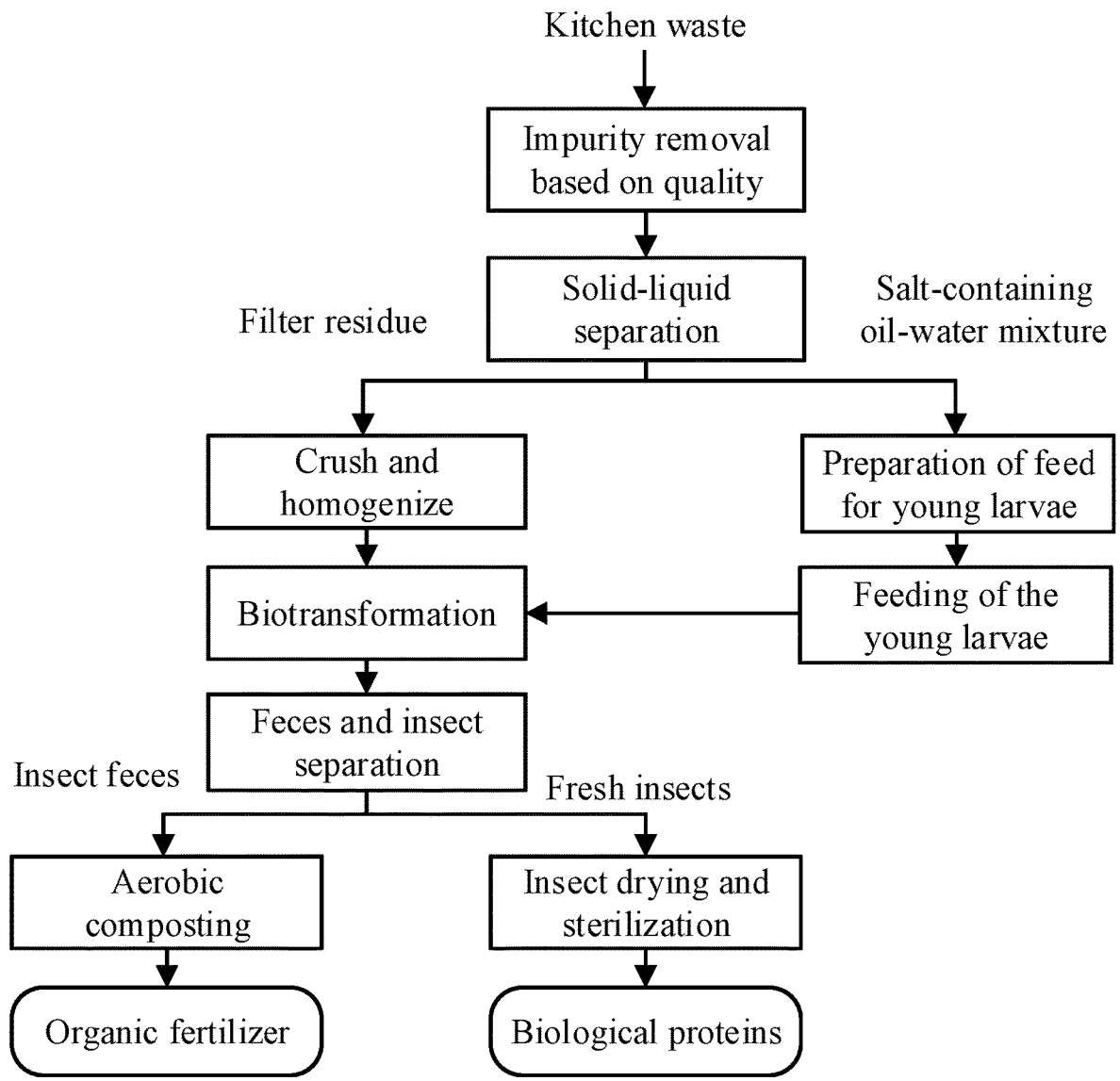
FIG. 1 is a flowchart of steps of a method for fully recycling kitchen waste by using *Hermetia illucens* L. and aerobic microorganisms according to the present application.

To make the objective and technical solutions of embodiments of the present application clearer, the technical solutions of the embodiments of the present application are clearly and completely described below with reference to the accompanying drawings in the embodiments of the present application. Obviously, the described embodiments are some but not all of the embodiments of the present application. All other embodiments obtained by a person of ordinary skill in the art based on the embodiments of the present invention without creative efforts shall fall within the protection scope of the present application.

It can be understood by a person skilled in the art that, unless otherwise defined, all terms used herein (including technical terms and scientific terms) have the same meanings as those generally understood by a person of ordinary skill in the art to which the present application belongs. It should also be understood that terms such as those defined in universal dictionaries should be understood as having meanings consistent with those in the context of the existing technologies, and will not be interpreted with idealized or overly formal meanings unless defined as herein.

In an existing kitchen waste treatment technology, the bottleneck of a transformation rate of the technology mainly lies in the fact that an excessive salt content of materials affects utilization of fertilizer products, and it is difficult to recover high-salt wastewater. Therefore, in the present application, through solid-liquid separation pretreatment of kitchen waste, kitchen waste filter residue with the water content not greater than 75% and an oil-containing and salt-containing filtrate are obtained, so that 25% of salt in original kitchen waste is transferred to the oil-containing and salt-containing filtrate, and only 75% of the salt content of the original kitchen waste is retained in the kitchen waste filter residue used for feeding Hermetia illucens L. larvae, to adjust the water, oil and salt content of the filter residue to a more palatable range, so as to increase the transformation rate of Hermetia illucens L. larvae. In the present application, wheat bran and Hermetia illucens L. eggs may be mixed with the separated oil-containing and salt-containing filtrate, and the mixture is directly supplied to young larvae hatched from the eggs. After the young larvae grow into Hermetia illucens L. larvae, the Hermetia illucens L. larvae are fed with kitchen waste filter residue slurry, and the insect feces obtained by transabdominal transformation by the Hermetia illucens L. larvae are removed regularly. Therefore, in the present application, about 63% of the salt in the original kitchen waste is transferred to body fluid of the Hermetia illucens L. larvae by feeding with materials in an early Hermetia illucens L. hatching stage and a subsequent stage, and a salt conversion rate is increased by 14.5% compared with 55% in the existing technologies. Therefore, the salt content in the feces of Hermetia illucens L. can be reduced from 20% in the existing technologies to about 12%, so as to resolve the problem that the composting treatment of high-salt materials is not up to standard. The timely separated insect feces may be directly sent to an aerobic microbial degradation apparatus in batches for aerobic composting to obtain an organic fertilizer; and after the Hermetia illucens L. larvae grow to the $5^{th}$-$6^{th}$ instars, Hermetia illucens L. insects may be directly screened out, and are dried and sterilized to obtain dried insects to implement biomass reuse.

A specific test process of the foregoing process steps is as follows.

Embodiment 1

As shown in FIG. 1, kitchen waste is treated according to the following steps. Step (1): Solid-liquid separation pretreatment of kitchen waste: During treatment, inert impurities in kitchen waste can be first removed by magnetic separation and separation by using a roller, and then solid-liquid separation is performed by pressure filtration, so that a water content of kitchen waste filter residue is controlled to be no more than 70%, then salinity thereof is adjusted to about 3%, and an oil content thereof is adjusted to about 5.2%; and the kitchen waste filter residue is crushed and homogenized to form slurry with a particle size of 3-8 mm. Oil-water separation is performed on the kitchen waste filtrate by standing separation, so that the salinity of separated kitchen waste filtrate is adjusted to about 5.8%, and an oil content is controlled at about 9.2%.

Step (2): Separately perform resource utilization of filtrate and filter residue:

On the one hand, the oil-containing and salt-containing filtrate is used to feed young larvae of Hermetia illucens L. During the operation, the salt-containing oil-water mixture, wheat bran and Hermetia illucens L. eggs are preferably mixed at a mass ratio of 32:20:1, the humidity of the mixture of the salt-containing oil-water mixture and the wheat bran is controlled at 65%, and larvae can grow into $2^{nd}$-instar Hermetia illucens L. larvae after feeding for 5 days.

On the other hand, the kitchen waste filter residue is transabdominally transformed by using Hermetia illucens L. During the operation, preferably, the kitchen waste filter residue slurry with a corresponding ratio is evenly added to a transabdominal transformation biological reaction chamber accommodating the Hermetia illucens L. larvae three times a day at a ratio of correspondingly adding 900-1100 g of kitchen waste filter residue slurry to every gram of larvae every day, with an interval of 6 hours between feedings. During the process, exhausting is kept for 20 minutes every hour, and turning is performed once every 6 hours, so that the temperature of a material layer is controlled to be kept at 28° C.-32° C., the air humidity is kept at 60%, and the oxygen content of the material layer is kept at 15% or above.

Step (3): Separation of Hermetia illucens L. insects and insect feces residue: Hermetia illucens L. larvae and insect feces in the transabdominal transformation biological reaction chamber are screened before the kitchen waste slurry is added every day. During the screening, the mixture of the larvae and the insect feces is separated by vibration based on a particle size difference. Hermetia illucens L. larvae that do not reach the $5^{th}$-instar or $6^{th}$-instar are screened out and put into the transabdominal transformation biological reaction chamber again for feeding, and the separated insect feces are sent to an aerobic microbial degradation apparatus. After feeding for 13-14 days, when the Hermetia illucens L. larvae grow to the $6^{th}$ instar, before the screening operation, Hermetia illucens L. is starved for 6-8 hours to ensure that the kitchen filter residue is fully transformed, and a situation is prevented that remaining kitchen residue is still not transformed before the screening operation. Hermetia illucens L. screened out in this case is dried and sterilized to obtain dried insects to implement biological protein transformation.

Step (4): An organic fertilizer is produced by mixing insect feces with auxiliary materials in the aerobic microbial degradation apparatus: The insect feces obtained in step (3) undergo aerobic composting, and a high-quality organic fertilizer is obtained through microbial degradation. When the oxygen content of compost is controlled in a stable range, the total content of nitrogen, phosphorus and potassium in the obtained organic fertilizer product is 15%, and a seed germination index corresponding to the fertilizer is 85%, so that the organic fertilizer with higher quality and lower salinity can be obtained.

in step (3), after *Hermetia illucens* L. is fed to grow for 15-16 days, $6^{th}$-instar insects are separated, and the insects are dried and sterilized to obtain dried insects.

The remaining is the same as that of Embodiment 1.

Kitchen waste treatment efficiency, product yield and quality parameters corresponding to Embodiments 1-3 and the comparative example were tested and counted, and results shown in Table 1 were obtained.

TABLE 1

| Index | Embodiment 1 | Embodiment 2 | Embodiment 3 | Comparative example |
|---|---|---|---|---|
| Kitchen waste treatment efficiency (kg of kitchen waste/g of eggs/day) | 1.1 | 1 | 0.9 | 0.65 |
| Growth time (day) of *Hermetia illucens* L. at $2^{nd}$-$6^{th}$ instars | 12-13 | 13-14 | 14-15 | 15-16 |
| Weight of a hundred of *Hermetia illucens* L. (fresh weight, g) | 15-20 | 14-18 | 16-19 | 11-14 |
| Insect yield per ton of kitchen waste (fresh weight, %) | 25-30 | 16-18 | 20-22 | 12-15 |
| Fertilizer yield per ton of kitchen waste (fresh weight, %) | 16-19 | 12-14 | 14-16 | 10-15 |

Embodiment 2

This embodiment has the same operation steps of a transformation process as Embodiment 1 only except that:
in step (1), the water content of the kitchen filter residue is adjusted to be not greater than 65%, the salinity is 2.8%, and the oil content is 2.6%;
in step (2), the feeding ratio of kitchen filter residue is adjusted to 1 kg of kitchen filter residue:1 g of larvae hatched from eggs; and
in step (3), after *Hermetia illucens* L. is fed to grow for 13-14 days, $6^{th}$-instar insects are dried and sterilized to obtain dried insects.
The remaining is the same as that of Embodiment 1.

Embodiment 3

This embodiment has the same operation steps of a transformation process as Embodiment 1 only except that:
in step (1), the water content of the kitchen filter residue is adjusted to be not greater than 75%, the salinity is 3.2%, and the oil content is 14.5%;
in step (2), the feeding ratio of kitchen filter residue is adjusted to 0.9 kg of kitchen filter residue:1 g of larvae hatched from eggs; and
in step (3), after *Hermetia illucens* L. is fed to grow for 14-15 days, $6^{th}$-instar insects are dried and sterilized to obtain dried insects.
The remaining is the same as that of Embodiment 1.

Comparative Example

This comparative example has the same operation steps of a transformation process as Embodiments 1 to 3 and differs from Embodiment 1 only in that:
in step (1), the water content of kitchen filter residue is increased to 80%;
in step (2), the feeding ratio of kitchen filter residue is adjusted to 0.65 kg of kitchen filter residue:1 g of larvae hatched from eggs; and It can be learned from Table 1 that in Embodiments 1-3, because the oil, salt and water contents of the kitchen filter residue are controlled, and the daily separation of insect feces is implemented, the kitchen waste treatment efficiency, the yield and monomer mass of *Hermetia illucens* L., and the yield of insect manure compost are all higher than those of the comparative example.

The contents of oil, salt and water in Embodiment 1 are within the preferable feeding palatability range by pressure filtration, so as to improve the feeding of *Hermetia illucens* L. and increase a kitchen waste treatment speed. In specific operation, the water content of kitchen waste can be controlled by pressure filtration in each embodiment, and the oil content and the salt content change correspondingly after the water content is controlled. The ranges of oil and salt in the patent are the corresponding ranges after the water content is controlled, and if the oil content is excessive, the oil may be further separated by standing.

By adjusting the ratio of oil, salt and water in the feed materials, the feeding efficiency of *Hermetia illucens* L. is changed based on its growth and diet habits: (1) The ratio of the kitchen waste filter residue slurry is adjusted to an appropriate oil-salt range that accords with an optimal feeding rate of *Hermetia illucens* L., so as to prevent a case that the excessive/too low oil-salt content in the comparative example reduces the palatability of the kitchen waste, thereby affecting the feeding rate of larvae. (2) The water content of the kitchen waste filter residue slurry is adjusted to a suitable range which accords with the optimal feeding rate of *Hermetia illucens* L., and the survival and growth of *Hermetia illucens* L. are affected by adjusting the oxygen content and temperature of the materials, so as to obtain a relatively optimal transformation effect in Embodiment 1.

The organic fertilizers produced by composting of insect feces in Embodiments 1-3 and the comparative example were tested according to NY/T 525-2021 test index determining standards, and results shown in Table 2 were obtained.

TABLE 2

| Index | Embodiment 1 | Embodiment 2 | Embodiment 3 | Comparative example | Standard limit value |
|---|---|---|---|---|---|
| Organic matter, % | 58.6 | 55.3 | 56.4 | 55.9 | ≥30 |
| Water content, % | 27.6 | 29.3 | 28.2 | 29.6 | ≤30 |
| pH | 7.6 | 7.58 | 7.65 | 7.45 | 5.5-8.5 |
| Total nutrients, % | 4.69 | 4.58 | 4.63 | 4.48 | ≥4.0 |
| Seed germination index, % | 85 | 82 | 83 | 0 | ≥70 |
| Total water-soluble salt, g/kg | 60.7 | 61.3 | 63.6 | 112 | / |
| Mass fraction of mechanical impurities, % | 0 | 0 | 0 | 0 | ≤0.5 |

It can be learned from Table 2 that the technical indexes of organic fertilizer of insect feces in Embodiments 1, 2 and 3 all meet requirements of NY/T 525-2021, while the seed germination index of the comparative example is 0. This is because no daily separation of insects from feces is performed in the comparative example, the kitchen filter residue which has not undergone transabdominal transformation is mixed in the insect feces, and the insect feces contain more salt.

Figure 2:
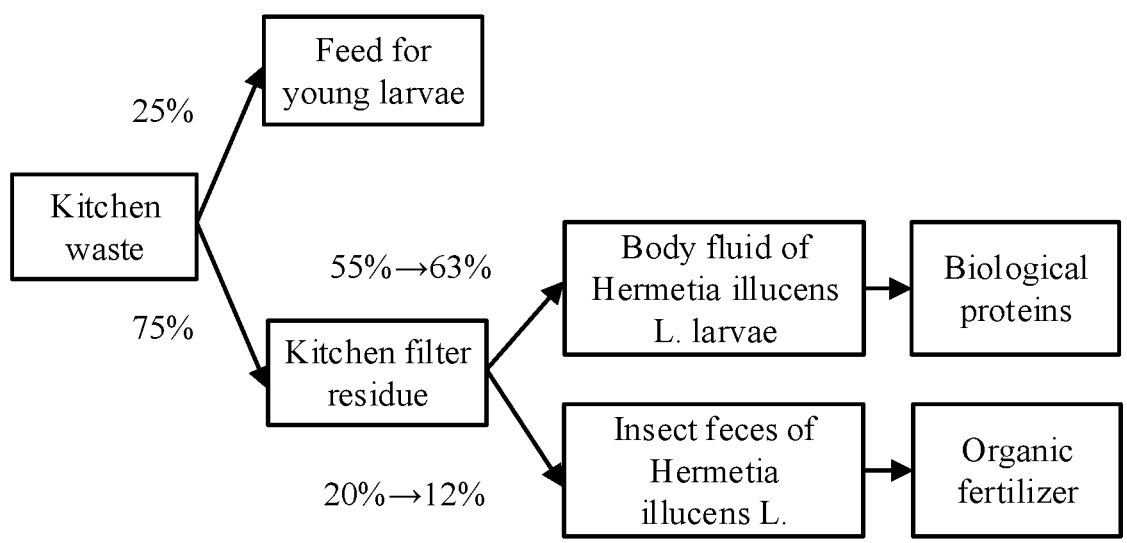
FIG. 2 is a path diagram of salt metabolism in a process according to the present application.

Further referring to the salt metabolism transfer ratio in FIG. 2 (the percentage value indicates the proportion of the mass of salt of the product on the right side of the arrow in the mass of salt of kitchen waste), it can be learned that in this study, by controlling the distribution ratio of kitchen waste water, salt and oil in kitchen solid residue and the salt-containing oil-water mixture in step (1), the kitchen filter residue has better palatability to *Hermetia illucens* L., and can further improve the content of nutrients (including salt) taken by *Hermetia illucens* L. from the kitchen filter residue. The adjustment and control of the oil-salt ratio of feed materials avoids the generation of a large amount of high-salt wastewater which cannot be avoided in existing technologies, and simplifies a system for sewage treatment of high-salt wastewater. After mixing of the salt-containing oil-water mixture with wheat bran, etc., proteins and lipid in feed for young larvae can be further added, the yield of *Hermetia illucens* L. larvae is improved, and the salt content in *Hermetia illucens* L. feces is reduced. In addition, step (3) reduces the kitchen solid residue mixed in the insect feces without transabdominal transformation, the salt content of the insect feces is further reduced, and utilization of nutrients in the kitchen waste is improved.

Therefore, in the present application, by performing solid-liquid separation on the kitchen waste, the kitchen waste filter residue and the oil-containing and salt-containing filtrate are used to feed the young larvae and the *Hermetia illucens* L. larvae respectively, so that most of the salt in the kitchen waste can be transferred to the body fluid of the *Hermetia illucens* L. larvae to form electrolyte. Organic matter such as proteins and fat in the kitchen waste is transformed into biological proteins by using the subsequent process of transabdominal transformation by the *Hermetia illucens* L. larvae, and the salt content of the insect feces is effectively reduced by daily screening. The organic fertilizer prepared by composting of the insect feces can meet relevant standards, thereby resolving the following problems encountered with in the existing treatment technology.

(1) As high-salt wastewater, an oil-salt-water mixture filtered out from kitchen waste has high treatment costs and treatment difficulty. The mixing of the oil-salt-water mixture with wheat bran to prepare feed for young larvae of *Hermetia illucens* L. can implement resource utilization of oil-containing and salt-containing wastewater and significantly reduce feeding costs.

(2) By using a simple low-cost method such as pressure filtration and standing separation, the water, salt and oil contents of the kitchen waste filter residue after solid-liquid separation can be adjusted to a palatable proportion suitable for feeding of *Hermetia illucens* L. larvae, which can improve transabdominal transformation efficiency of *Hermetia illucens* L. and improve the growth of *Hermetia illucens* L. insects.

(3) The growth characteristics of *Hermetia illucens* L. are used to transform the salt in kitchen waste into the body fluid of *Hermetia illucens* L., and on this basis, the insect feces are further separated from the insects on the same day to further resolve the problem that the excessive salt in the original insect feces affects the quality of a compost fertilizer.

(4) By separating the insects from the insect feces on the same day, and controlling the oxygen content of a material layer, anaerobic composting conditions are avoided, so as to reduce the generation amount of nitrogen-containing odor, prevent the nitrogen loss caused by the anaerobic environment during transformation by *Hermetia illucens* L., improve nutrient utilization, and increase the yield of products obtained by the transformation of kitchen waste in unit weight.

The above are only the implementations of the present application, and descriptions thereof are relatively specific and detailed, but the implementations should not be construed as limiting the patent scope of the present application. It should be noted that for a person of ordinary skill in the art, several modifications and improvements can be further made without departing from the conception of the present application, and shall fall within the protection scope of the present application.

What is claimed is:

1. A method for fully recycling kitchen waste by using *Hermetia illucens* L. and aerobic microorganisms, comprising the following steps:

step 1: removing inert impurities in the kitchen waste by magnetic separation and separation by using a roller, and then performing solid-liquid separation to obtain kitchen waste filter residue and an oil-containing and salt-containing filtrate;

controlling a water content of the kitchen waste filter residue to be no more than 75% by pressure filtration, so that salinity is adjusted to 2.8%-3.2%, and an oil content is controlled at 2.6%-15%;

performing oil-water separation on the kitchen waste filter residue by standing separation, so that salinity of the oil-containing and salt-containing filtrate is controlled at 5.5%-6.5%, and an oil content is controlled at 3.4%-15%; and then crushing and homogenizing the kitchen waste filter residue to form slurry with a particle size of 3-8 mm;

step 2: mixing wheat bran with the oil-containing and salt-containing filtrate to feed young larvae hatched from eggs, wherein a mass ratio of the oil-containing and salt-containing filtrate, the wheat bran, and the *Hermetia illucens* L. eggs is (32-35):(18-20):1, and a humidity of a mixed material is controlled at 60%-70%; and feeding young larvae hatched from *Hermetia illucens* L. eggs with the mixed material for 5-7 days to obtain $2^{nd}$-$3^{rd}$ instar *Hermetia illucens* L. larvae; after the young larvae grow into the *Hermetia illucens* L. larvae, using the kitchen waste filter residue instead to feed the *Hermetia illucens* L. larvae evenly in batches at a ratio of correspondingly adding 900-1100 g of kitchen waste filter residue slurry to every gram of *Hermetia illucens* L. larvae every day, regularly exhausting and turning to control temperature and humidity, screening a mixture of the *Hermetia illucens* L. larvae and insect feces every day to obtain *Hermetia illucens* L. larvae and insect feces, and continuing to feed the *Hermetia illucens* L. larvae screened with the kitchen waste; and step 3: sending the separated insect feces to an aerobic microbial degradation apparatus for aerobic composting to obtain an organic fertilizer; and after the *Hermetia illucens* L. larvae grow to the $5^{th}$-$6^{th}$ instars, screening out *Hermetia illucens* L. insects, and drying and sterilizing the *Hermetia illucens* L. insects to obtain dried insects.

2. The method for fully recycling kitchen waste by using *Hermetia illucens* L. and aerobic microorganisms according to claim 1, wherein the water content of the kitchen waste filter residue is controlled to be no more than 70%, the salinity thereof is 3%, and the oil content thereof is 5.2%; and after standing, through oil-water separation of the oil-containing and salt-containing filtrate, the salinity of the oil-containing and salt-containing filtrate is adjusted to 5.8%, and the oil content thereof is adjusted to 9.2%.

3. The method for fully recycling kitchen waste by using *Hermetia illucens* L. and aerobic microorganisms according to claim 1, wherein the mass ratio of the oil-containing and salt-containing filtrate, the wheat bran, and the *Hermetia illucens* L. eggs is 32:20:1, and the humidity of the mixed material is controlled at 65%; and after the young larvae of *Hermetia illucens* L. are fed for 5 days, $2^{nd}$-instar *Hermetia illucens* L. larvae are obtained, and then the *Hermetia illucens* L. larvae are fed with the kitchen waste filter residue slurry.

4. The method for fully recycling kitchen waste by using *Hermetia illucens* L. and aerobic microorganisms according to claim 1, wherein in step 2, the feeding evenly in batches at a ratio of correspondingly adding 900-1100 g of kitchen waste filter residue slurry to every gram of *Hermetia illucens* L. larvae every day comprises:

evenly adding 225-366 g of kitchen waste filter residue slurry to each gram of *Hermetia illucens* L. larvae at intervals of 6-8 hours for 3-4 times every day.

5. The method for fully recycling kitchen waste by using *Hermetia illucens* L. and aerobic microorganisms according to claim 4, wherein in step 2, the feeding evenly in batches at a ratio of correspondingly adding 900-1100 g of kitchen waste filter residue slurry to every gram of *Hermetia illucens* L. larvae every day comprises:

evenly adding 300-366 g of kitchen waste filter residue slurry to each gram of *Hermetia illucens* L. larvae at intervals of 6 hours for 3 times every day.

6. The method for fully recycling kitchen waste by using *Hermetia illucens* L. and aerobic microorganisms according to claim 5, wherein in step 2, a standard for regularly exhausting and turning to control temperature and humidity is that exhausting is performed for 20 minutes every hour, turning is performed once every 6 hours, so that the temperature of a feeding layer is controlled to be kept at 28-32° C., the air humidity in a transabdominal transformation biological reaction chamber is controlled to be kept at 60%, and an oxygen content of the feeding layer is kept at 15% or above.

7. The method for fully recycling kitchen waste by using *Hermetia illucens* L. and aerobic microorganisms according to claim 5, wherein in step 2, within 10-12 days after the *Hermetia illucens* L. larvae are added, the mixture of the *Hermetia illucens* L. insects and the insect feces is screened every day, and the *Hermetia illucens* L. larvae are returned to the transabdominal transformation biological reaction chamber after screening for continued feeding; and within 13-14 days after the *Hermetia illucens* L. larvae are added, the *Hermetia illucens* L. larvae are starved before the mixture of the insects and the insect feces is screened, and the *Hermetia illucens* L. insects are dried and sterilized to obtain the dried insects after screening.

\* \* \* \* \*